United States Patent [19]

Byers

[11] Patent Number: 4,814,281

[45] Date of Patent: Mar. 21, 1989

[54] DIFFERENTIAL CONDUCTIVITY SULFATE MONITOR

[75] Inventor: William A. Byers, Penn Hills Township, Allegheny County, Pa.

[73] Assignee: Westinghouse Electric Corp., Pittsburgh, Pa.

[21] Appl. No.: 191,814

[22] Filed: May 6, 1988

Related U.S. Application Data

[63] Continuation of Ser. No. 817,186, Jan. 7, 1986, abandoned.

[51] Int. Cl.$^4$ .................. G01N 1/18; G01N 27/00
[52] U.S. Cl. ................................. 436/150; 436/119; 436/151; 436/161; 436/178; 422/62; 422/68; 422/70; 422/76
[58] Field of Search ............... 422/62, 68, 70, 76, 422/119; 436/119, 120, 150, 151, 161, 178

[56] References Cited

U.S. PATENT DOCUMENTS

| | | | |
|---|---|---|---|
| 2,832,673 | 4/1958 | Larson et al. | 436/150 X |
| 2,950,176 | 8/1960 | Thayer et al. | 436/150 |
| 3,468,764 | 9/1969 | Cohen et al. | |
| 3,622,277 | 11/1971 | Noll. | |
| 4,242,097 | 12/1980 | Rich, Jr. et al. | 422/70 X |
| 4,251,219 | 2/1981 | Larson et al. | |
| 4,251,220 | 2/1981 | Larson et al. | 422/76 X |
| 4,272,246 | 6/1981 | Fritz et al. | |
| 4,290,775 | 9/1981 | Stevens et al. | 436/150 |
| 4,622,306 | 11/1986 | Düve | 436/150 |
| 4,699,718 | 10/1987 | Jones et al. | 422/70 X |
| 4,732,686 | 3/1988 | Small et al. | 436/150 X |

*Primary Examiner*—Michael S. Marcus
*Assistant Examiner*—Lynn Kummert

[57] ABSTRACT

A differential conductivity sulfate monitor for determining the sulfate concentration of a fluid sample by monitoring the cation conductivity of the fluid sample before and after sulfate has been removed therefrom. The cation conductivities of the fluid sample before and after sulfate has been removed are compared to establish a differential conductivity, and the differential conductivity is used to calculate the sulfate concentration in accordance with a known relationship between a conductivity differential and the sulfate concentration of a fluid sample.

18 Claims, 2 Drawing Sheets

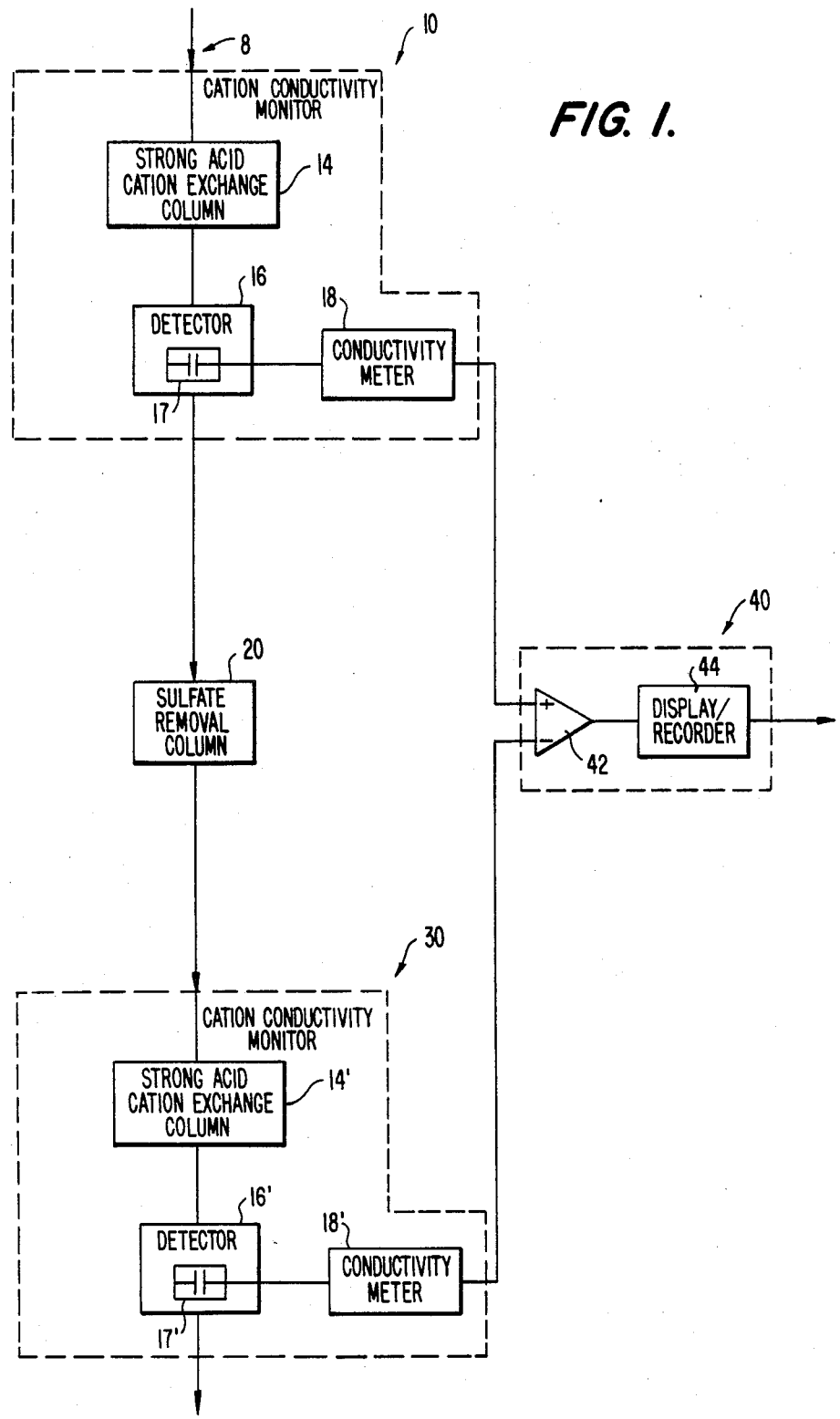

4,814,281

DIFFERENTIAL CONDUCTIVITY SULFATE MONITOR

This application is a continuation of application Ser. No. 06/817,186 filed Jan. 7, 1986, now abandoned.

BACKGROUND OF THE INVENTION

1. Field of the Invention

The present invention relates to a monitor for determining the concentration of sulfate ($SO_4$) in a fluid sample stream, and more particularly, a continuous on-line differential conductivity monitor for measuring trace sulfate impurities.

2. Description of the Related Art

Sulfate is one of the most common contaminants in the steam cycle water of fossil and nuclear fueled power generating plants. Sources of sulfate in steam cycle water are condenser inleakage, ion exchange resin ingress, and improper regeneration of condensate polishers with sulfuric acid. Non-volatile impurities, particularly sulfate, concentrate quickly on turbine blades and in "dry-out" regions of a boiler or steam generator. The concentrated impurities can lead to accelerated corrosion and/or a loss in operating efficiency. Thus, there is a need to monitor the sulfate concentration of steam cycle water.

Sulfate (sulfuric acid) is one of the main components of acid precipitation (acid rain) and is present as a consequence of the burning of sulfur containing fossil fuels. Damage to the environment from acid rain has been well documented, but is not completely understood. The ability to continuously monitor natural waters affected by acid rain for sulfate will further the understanding of the problems associated with acid rain and facilitate regulation of acid rain pollution.

The various techniques for monitoring sulfate are as follows:

Cation conductivity, the electrical conductivity of a fluid sample that has been passed through a cation exchange column in the $H^+$ form, is a sensitive method for continuously monitoring anionic impurities. Cation conductivity measurements, however, do not determine the concentration of individual impurities or contaminants in a fluid sample.

Ion chromatography is a sensitive and specific technique for sulfate monitoring, but, ion chromatographs are, by their nature, non-continuous monitors. Further, the hardware required for ion chromatography is both complex and expensive.

The methylthymol blue flow injection method is sensitive in a range of 100 ppb to 6000 ppb. This measurement range may be satisfactory for some acid rain measurements, but it does not provide monitoring in the 0-100 ppb range necessary to monitor sulfate in the steam cycle water of a power generating plant.

U.S. Pat. No. 4,251,219, Larson et at., discloses an apparatus for monitoring the purity of condensate in boiler systems, such as steam power plants and pressurized water reactor nuclear systems. The apparatus passes condensate through a hydrogen exchange resin bed and heats the effluent from the resin bed to the atmospheric boiling point temperature. The conductivity of the heated effluent is measured at or close to the atmospheric boiling point temperature and is an indication of the concentrations of chloride, sulfate, phosphate, nitrate, and other inorganic anions, in relatively low pressure condensate. This apparatus, however, relies on a conductivity measurement which does not determine the concentration of the individual impurities or contaminants.

SUMMARY OF THE INVENTION

It is an object of the present invention to provide a continuous on-line monitor for specifically measuring low level concentrations of sulfate.

A continuous on-line sulfate monitor in accordance with the present invention measures the cation conductivity of an influent fluid sample stream before and after sulfate is removed from the influent fluid sample stream. Cation conductivity signals representative of the cation conductivities before and after sulfate removal are compared, and a differential conductivity, the difference between the two cation conductivities, can be directly related to the sulfate concentration of the influent fluid sample stream.

The differential conductivity sulfate monitor of the present invention includes a first cation conductivity monitor for monitoring the cation conductivity of an influent fluid sample stream. A sulfate removal column containing a macroreticular weak acid cation exchange resin in the mixed $Ba^{++}$ and $H^+$ form removes sulfate from the fluid sample stream which has been monitored by the first cation conductivity monitor. A second cation conductivity monitor monitors the cation conductivity of the fluid sample stream from which first and second cation conductivity signals, generated by the first and second cation conductivity monitors, are supplied to a differential amplifier which generates a differential conductivity signal corresponding to the difference in the cation conductivities before and after sulfate has been removed from the fluid sample. The sulfate concentration of the influent sample stream is determined in accordance with the differential conductivity by a meter which is calibrated using a known relationship between the sulfate concentration of a fluid sample and a differential conductivity.

BRIEF DESCRIPTION OF THE DRAWINGS

FIG. 1 is a schematic diagram of a differential conductivity sulfate monitor in accordance with the present invention;

DESCRIPTION OF THE PREFERRED EMBODIMENT

Figure 3:
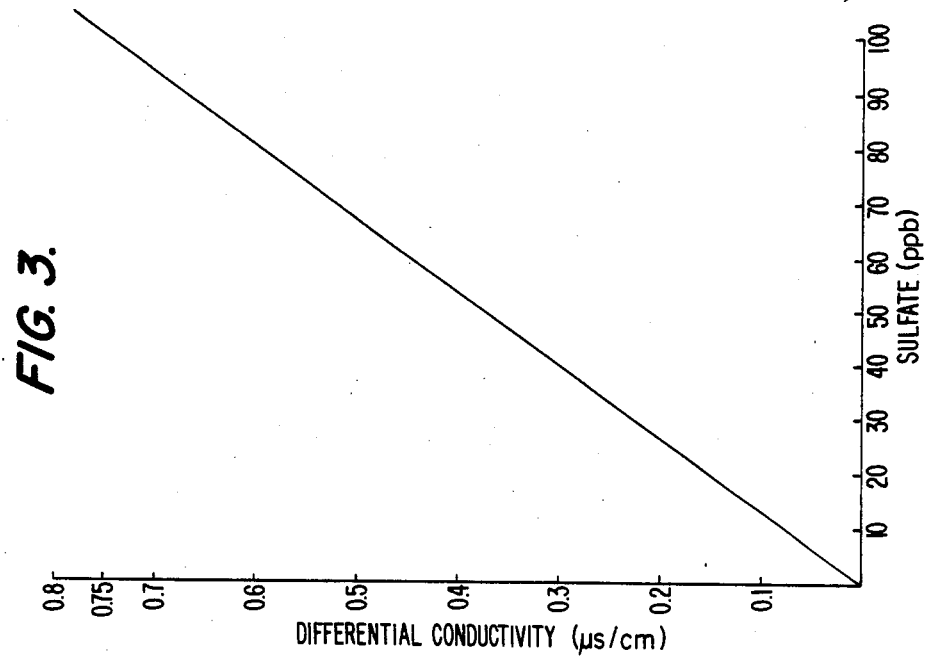
FIG. 3 is a graph representing the relationship between a differential conductivity and sulfate concentration.

FIG. 1 is a schematic diagram of a differential conductivity sulfate monitor in accordance with the present invention. The sulfate monitor includes a fluid line 8 for supplying an influent fluid sample stream of steam cycle water from a power plant steam cycle, or any other fluid sample for which the sulfate concentration is to be monitored. The fluid line 8 also interconnects various components of the sulfate monitor in a fluid series circuit. A first cation conductivity monitor 10 receives the influent fluid sample stream from the fluid line 8, monitors the cation conductivity of the influent fluid sample stream and provides a monitored fluid sample stream. The cation conductivity monitor 10 includes a strong acid cation exchange column 14, a detector 16 having a conductivity cell 17 for sensing the cation conductivity of the fluid sample stream passing from the strong acid cation exchange column 14 and generating a first cation conductivity signal representative of the sensed cation conductivity, and a conductivity meter 18 for displaying the cation conductivity monitored by the detector 16.

An influent fluid sample stream entering the first cation conductivity monitor 10, first passes through the strong acid cation exchange column 14 which contains a strong acid resin in the $H^+$ form (not shown). In the strong acid cation exchange column 14, cations in the sample are exchanged for hydrogen ion ($H^+$). The strong acid cation exchange column 14 provides a first altered fluid sample stream having cations removed therefrom, and thus the monitored fluid sample stream provided by the first cation conductivity montor 10 has cations removed therefrom. The exchange of cations for $H^+$ is necessary for several reasons. First, the conductance of $H^+$ is very high and the sensitivity of the cation conductivity measurement is increased. For example, the strong acid cation exchange column exchanges sodium (Na) in $Na_2SO_4$ for hydrogen (H) to provide $H_2SO_4$, thus increasing the conductivity because $H_2SO_4$ has a higher conductivity than $Na_2SO_4$. Second, the strong acid cation exchange column 14 removes ammonium hydroxide, a common additive in steam cycle water, from the influent fluid sample stream. The removal of ammonium hydroxide reduces the background conductivity and increases the signal-to-noise ratio of the cation conductivity signal. Third, the strong acid cation exchange column 14 functions to increase the life of a sulfate removal column 20 (described below) which is expended less rapidly if ammonium hydroxide is not passed through it. Fourth, the strong acid cation exchange 14 lowers the pH of the influent sample stream, thereby increasing the selectivity of the sulfate monitor for sulfate.

The conductivity cell 17 in the detector 16 is sufficiently sensitive to detect changes in conductivity of 0.002 $\mu S/cm$, so that sulfate levels in the low ppb range can be monitored. The conductivity cell 17 may be a model 4905-002-33-000-7 produced by Leeds & Northrup. The conductivity meter 18 may be any standard analog or digital meter, or a strip chart recorder, for displaying the cation conductivity monitored by the detector 16.

After the cation conductivity of the influent fluid sample stream is monitored by the first cation conductivity monitor 10, the monitored fluid sample stream is passed through the sulfate removal column 20. The sulfate removal column 20 contains a macroreticular weak acid cation exchange resin in the mixed $Ba^{++}$ and $H^+$ form. In the sulfate removal column 20 barium ions are exchanged with hydrogen ions in the fluid sample stream, and the barium ions react with any sulfate in the sample stream to form an insoluble $BaSO_4$ precipitate. The $BaSO_4$ precipitate is retained in the pores of the macroreticular resin, and thus sulfate is removed from the fluid sample stream to provide a fluid sample stream having sulfate removed therefrom. The macroreticular weak acid cation exchange resin may be Amberlite IRC-50, a resin in the $H^+$ form produced by Polysciences, Ltd. The weak acid cation exchange resin in the $H^+$ form is dosed with a solution containing barium, e.g., barium nitrate ($Ba(NO_3)_2$), barium chloride ($BaCl_2$) or barium hydroxide ($Ba(OH)_2$) to provide a resin in the mixed $Ba^{++}$ and $H^+$ form. The macroreticular weak acid cation exchange resin may also be adjusted to have a pH in the acid range by dosing with nitric acid.

A weak acid resin is used in the sulfate removal column 20 because of the order of selectivity of a weak acid resin for cations. In particular, the order of selectivity for a weak acid resin, from the strongest to the weakest interaction is $H > Fe > Ba\ Sr > Ca > Mg$. Thus, since the selectivity for $H^+$ is higher than $Ba^{++}$ in a weak acid resin, the hydrogen ions introduced to the fluid sample stream by the strong acid cation exchange column 14 in the first cation conductivity monitor 10 are exchanged with $Ba^{++}$ in the sulfate removal column 20, an interaction which would not be favorable on a strong acid resin. Further, the ratio of the ion exchange sites in a resin in the mixed $Ba^{++}$ and $H^+$ form should be adjusted so that an acidic local environment is created in the pores of the resin. The acidic local environment is necessary to maintain selectivity for barium sulfate precipitation and is provided by pH adjustment of the resin with nitric acid. If the pore environment in the resin is basic, barium carbonate, barium fluoride and barium phosphate are likely to precipitate, in addition to barium sulfate. Moreover, at a low pH, the solubility products for the non-sulfate barium salts are not likely to be exceeded.

The present invention contemplates the use of a sulfate removal column containing a weak acid resin in the mixed $Ba^{++}$ and $H^+$ form. It is to be unerstood, however, that other methods of removing sulfate from a fluid sample may be employed. For example, sulfate in the fluid sample stream could be precipitated and then filtered.

A second cation conductivity monitor 30 monitors the cation conductivity of the fluid sample having sulfate removed therefrom. The second cation conductivity monitor 30 is constructed in the same manner as the first cation conductivity monitor 10 and includes a strong acid exchange column 14', a detector 16' having conductivity cell 17', and a conductivity monitor 18'. The conductivity cell 17' is matched with the conductivity cell 17 of the first cation conductivity monitor 10, i.e., the cells have the same cell constant. The strong acid cation exchange column 14' exchanges any excess $Ba^{++}$ for $H^+$ so that all anions in the fluid sample have the same counter ion ($H^+$) as they did during the cation conductivity measurement by the first cation conductivity monitor 10. The strong acid cation exchange column 14' in the second cation monitor 30 provides a second altered fluid sample stream having cations, specifically barium, removed therefrom. The detector 16' in the second cation conductivity monitor 30 senses the cation conductivity of the second altered fluid sample stream and generates a second cation conductivity signal representative of the monitored cation conductivity. Conductivity meter 18' displays the cation conductivity monitored by the second cation conductivity monitor 30.

The conductivity meters 18 and 18' provide the first and second cation conductivity signals to a sulfate concentration determining unit 40 which determines the sulfate concentration in the influent fluid sample stream. The sulfate concentration determining unit 40 includes a differential amplifier 42 which generates a differential conductivity signal representative of the difference between the cation conductivity monitored by the first and second conductivity monitors 10 and 30. A display/recorder, or meter, 44 is calibrated to relate the differential conductivity signal to the sulfate concentration of the influent fluid sample stream. The display/recorder 44 may be a standard analog or digital meter or a strip chart recorder. Alternatively, the display recorder 44 may be a device which does not present a display but which generates a signal representative of the sulfate concentration of the influent fluid sample stream and provides the signal to the central computer (not shown) of a power generating plant.

The outputs from the first and second conductivity monitors 10 and 30 can alternatively be taken directly to a sulfate concentration determining unit comprising a computer, or microprocessor, (not shown) where the differential conductivity signal is generated and the sulfate concentration calculated in accordance with a relationship between the differential conductivity and a sulfate concentration. A further manner in which the differential conductivity signal can be generated is by placing the conductivity cells of the first and second conductivity monitors 10 and 30 in two arms of an AC bridge.

Figure 2:
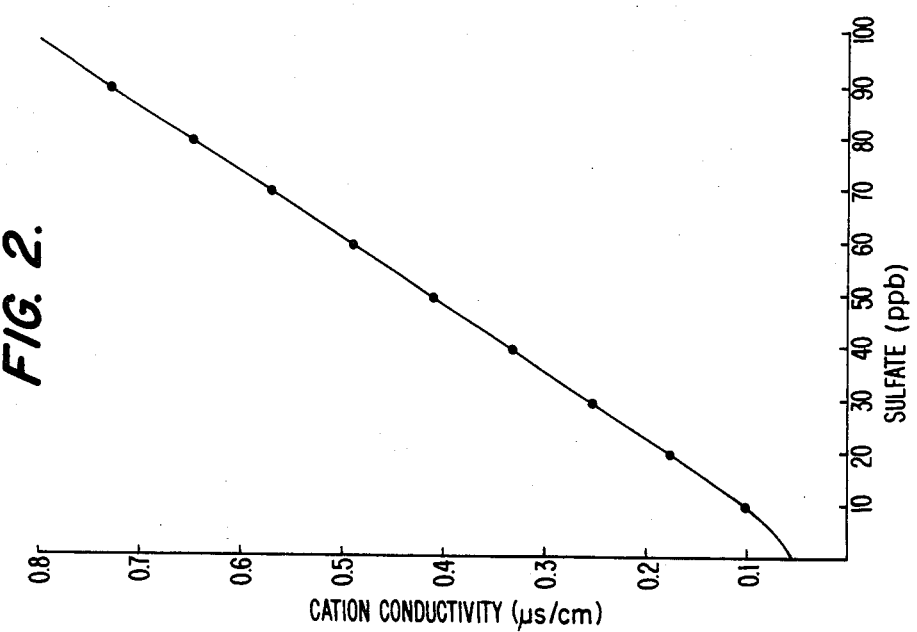
FIG. 2 is a graph representing the relationship between a cation conductivity and sulfate concentration.

FIG. 2 is a graph showing the relationship between the cation conductivity of a sample in $\mu S/cm$ and the sulfate concentration of the sample in ppb. FIG. 3 is a graph, derived from the graph in FIG. 2, showing the relationship between differential conductivity (the signal output by the differential amplifier 42) and sulfate concentration of a sample in ppb. The relationship between differential conductivity and sulfate concentration of a sample is used to calibrate the display/recorder 44 or any other device which is used to calculate the sulfate concentration in accordance with the first and second cation conductivity signals.

The many features and advantages of the differential conductivity sulfate monitor of the present invention will be readily apparent to those skilled in the art from the detailed specification. Accordingly, the claims are intended to cover all modifications falling within the true scope and spirit of the invention.

What is claimed is:

1. A method for continuously monitoring sulfate concentration in an aqueous stream containing a mixture of anions including sulfate ions comprising:
   measuring conductivity of an aqueous stream containing a mixture of anions including sulfate ions;
   selectively removing sulfate ions from the aqueous stream to present a sulfate free stream;
   measuring conductivity of the sulfate free stream; and
   comparing the measured conductivities as a function of sulfate concentration in the aqueous stream.

2. A method as set forth in claim 1 wherein said step of selectively removing sulfate ions is conducted utilizing a macroreticular weak acid cation exchange resin in the mixed $Ba^{++}$ and $H^+$ form.

3. A method as set forth in claim 2 wherein an acidic local environment is provided for said macroreticular weak acid cation exchange resin.

4. A method for continuously monitoring sulfate concentration in steam cycle water of a nuclear reactor system comprising:
   removing a sample stream of steam cycle water from a nuclear reactor system;
   removing cations other than $H^+$ ions from the sample stream and replacing the removed cations with $H^+$ ions utilizing strong acid cation exchange means to thereby present a strongly acid stream;
   measuring conductivity of the strongly acid stream;
   selectively removing sulfate ions from the strongly acid stream to present a sulfate free stream;
   measuring conductivity of the sulfate free stream; and
   comparing the measured conductivities as a function of sulfate concentration in the steam cycle water.

5. A method as set forth in claim 4 wherein said step of selectively removing sulfate ions is conducted utilizing a macroreticular weak acid cation exchange resin in the mixed $Ba^{++}$ and $H^+$ form.

6. A method as set forth in claim 5 wherein an acidic local environment is provided for said macroreticular weak acid cation exchange resin.

7. A method as set forth in claim 4 including the step of removing cations other than $H^+$ ions from the sulfate free stream and replacing the removed cations with $H^+$ ions utilizing a second strong acid cation exchange means to present a strongly acid sulfate free stream, said step of measuring conductivity of the sulfate free stream comprising measuring conductivity of the strongly acid sulfate free stream.

8. A method as set forth in claim 7 wherein said step of selectively removing sulfate ions is conducted utilizing a macroreticular weak acid cation exchange resin in the mixed $Ba^{++}$ and $H^+$ form.

9. A method as set forth in claim 8 wherein an acidic local environment is provided for said macroreticular weak acid cation exchange resin.

10. Apparatus for continuously monitoring sulfate concentration in an aqueous stream containing a mixture of anions including sulfate ions comprising:
    means for measuring conductivity of an aqueous stream containing a mixture of anions including sulfate ions;
    means for selectively removing sulfate ions from the aqueous stream to present a sulfate free stream;
    means for measuring conductivity of the sulfate free stream; and
    means for comparing the measured conductivities as a function of sulfate concentration in the aqueous stream.

11. Apparatus as set forth in claim 10 wherein said means for selectively removing sulfate ions comprises a macroreticular weak acid cation exchange resin in the mixed $Ba^{++}$ and $H^+$ form.

12. Apparatus as set forth in claim 11 wherein said macroreticular weak acid cation exchange resin has an acidic local environment.

13. Apparatus for continuously monitoring sulfate concentration in steam cycle water of a nuclear reactor system comprising:
    means for removing a sample stream of steam cycle water from a nuclear reactor system;
    strong acid cation exchange means for removing cations other than $H^+$ ions from the sample stream and replacing the removed cations with $H^+$ ions to present a strongly acid stream;
    first means for measuring conductivity of the strongly acid stream;
    means for selectively removing sulfate ions from the strongly acid stream to present a sulfate free stream;
    second means for measuring conductivity of the sulfate free stream; and
    means for comparing the measured conductivities as a function of sulfate concentration in the steam cycle water.

14. Apparatus as set forth in claim 13 wherein said means for selectively removing sulfate ions comprises a macroreticular weak acid cation exchange resin in the mixed $Ba^{++}$ and $H^+$ form.

15. Apparatus as set forth in claim 14 wherein said macroreticular weak acid cation exchange resin has an acidic local environment.

16. Apparatus as set forth in claim 13 including second strong acid cation exchange means interposed between the means for selectively removing sulfate ions and the second means for measuring conductivity, said second strong acid cation exchange means being positioned and arranged from removing cations other than H+ ions from the sulfate free stream and replacing the removed cations with H+ ions before the conductivity of the sulfate free stream is measured.

17. Apparatus as set forth in claim 16 wherein said means for selectively removing sulfate ions comprises a macroreticular weak acid cation exchange resin in the mixed $Ba^{++}$ and $H^+$ form.

18. Apparatus as set forth in claim 17 wherein said macroreticular weak acid cation exchange resin has an acidic local environment.

* * * * *